United States Patent
Geistert et al.

(10) Patent No.: US 10,045,706 B2
(45) Date of Patent: Aug. 14, 2018

(54) CATHETER AND METHOD FOR PRODUCING SAME

(71) Applicant: VascoMed GmbH, Binzen (DE)

(72) Inventors: Wolfgang Geistert, Rheinfelden (DE); Daniel Schulze, Zurich (CH)

(73) Assignee: VascoMed GmbH, Binzen (DE)

( * ) Notice: Subject to any disclaimer, the term of this patent is extended or adjusted under 35 U.S.C. 154(b) by 1023 days.

(21) Appl. No.: 14/294,327

(22) Filed: Jun. 3, 2014

(65) Prior Publication Data

US 2014/0378803 A1    Dec. 25, 2014

Related U.S. Application Data

(60) Provisional application No. 61/838,874, filed on Jun. 25, 2013.

(51) Int. Cl.
*A61B 5/042* (2006.01)
*A61N 1/05* (2006.01)
(Continued)

(52) U.S. Cl.
CPC ........ *A61B 5/0422* (2013.01); *A61B 18/1492* (2013.01); *A61M 25/001* (2013.01); *A61M 25/0009* (2013.01); *A61M 25/0045* (2013.01); *A61M 25/0067* (2013.01); *A61N 1/056* (2013.01); *A61B 2017/00526* (2013.01); *A61B 2562/125* (2013.01); *Y10T 156/1038* (2015.01)

(58) Field of Classification Search
CPC .............. A61B 5/0422; A61B 18/1492; A61B 2017/00526; A61B 2562/125; A61M 25/0009; A61M 25/001; Y10T 156/1038; A61N 1/056

USPC ..................................... 600/373–375; 29/825
See application file for complete search history.

(56) References Cited

U.S. PATENT DOCUMENTS 5,156,151 A * 10/1992 Imran ................... A61N 1/056
                                                              600/375
5,239,999 A    8/1993 Imran
(Continued)

FOREIGN PATENT DOCUMENTS

DE        4211852      1/1993
EP        0779059      6/1997

OTHER PUBLICATIONS

European Search Report and Notes to the European Search Report on European Patent Application No. EP 14 17 0181, dated Jul. 22, 2014 (5 pages).

*Primary Examiner* — Lee S Cohen
*Assistant Examiner* — Erin M Cardinal
(74) *Attorney, Agent, or Firm* — Buchanan Ingersoll & Rooney PC

(57) ABSTRACT

A catheter with a film composite structure. The catheter at least includes a polymer film that is shaped such that a first polymer film layer, which is arranged inwardly relative to the catheter, and a second polymer film layer, which is arranged outwardly relative to the catheter, are produced; one or more electrodes arranged at least partially on an outer surface of the film composite structure; and a conductor structure, which includes conductive tracks for the electrical connection of the electrodes and which is arranged at least in part between the first and second polymer film layers. An associated production method for the catheter is also contemplated herein.

17 Claims, 2 Drawing Sheets

(51) Int. Cl.
*A61M 25/00* (2006.01)
*A61B 18/14* (2006.01)
*A61B 17/00* (2006.01)

(56) References Cited

U.S. PATENT DOCUMENTS

| | | | | |
|---|---|---|---|---|
| 6,024,702 | A * | 2/2000 | Iversen | A61B 5/0422 600/378 |
| 6,210,339 | B1 * | 4/2001 | Kiepen | A61B 5/0215 600/372 |
| 2007/0219551 | A1 * | 9/2007 | Honour | A61B 5/0422 606/41 |
| 2008/0058912 | A1 * | 3/2008 | O'Brien | A61N 1/05 607/116 |
| 2009/0143651 | A1 * | 6/2009 | Kallback | A61B 5/02007 600/301 |
| 2009/0171274 | A1 * | 7/2009 | Harlev | A61B 5/0422 604/95.04 |
| 2009/0248122 | A1 * | 10/2009 | Pianca | A61N 1/0551 607/115 |
| 2010/0094279 | A1 * | 4/2010 | Kauphusman | A61B 5/0422 606/41 |
| 2010/0168647 | A1 * | 7/2010 | Tegg | A61B 18/1492 604/21 |
| 2010/0217257 | A1 | 8/2010 | Howat et al. | |
| 2012/0271138 | A1 * | 10/2012 | Kordis | A61B 5/0422 600/375 |
| 2014/0276789 | A1 * | 9/2014 | Dandler | A61B 18/1492 606/41 |

\* cited by examiner

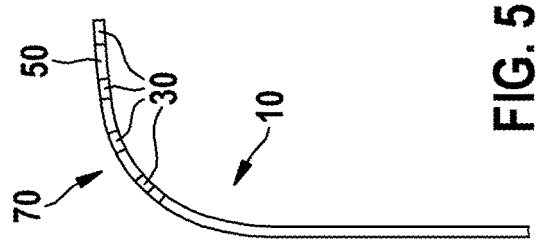
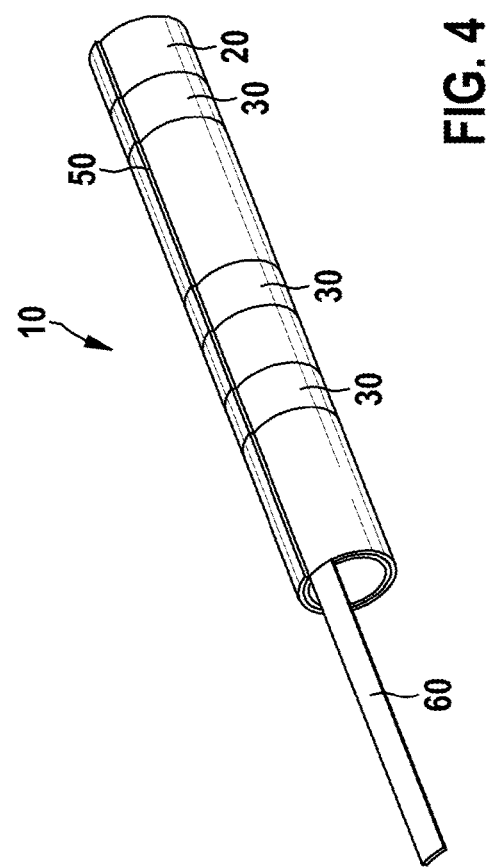
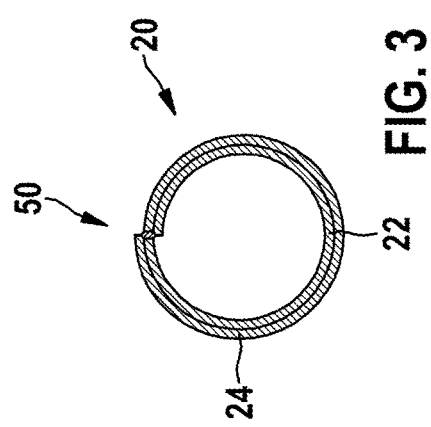

CATHETER AND METHOD FOR PRODUCING SAME

CROSS-REFERENCE TO RELATED APPLICATIONS

This patent application claims the benefit of U.S. Provisional Patent Application No. 61/838,874, filed on Jun. 25, 2013, the disclosure of which is hereby incorporated by reference in its entirety.

TECHNICAL FIELD

The present invention relates generally to a catheter and, in particular, to a cardiac catheter or vascular catheter, and to a method for producing the same.

BACKGROUND

Cardiac or vascular catheter examinations are minimally invasive medical examinations of the heart using a catheter, which is typically introduced via veins or arteries at the groin, the bend of the elbow, or via the wrist joint. Depending on the objective of the examination, different points in the heart or the coronary vessels or the peripheral vessels are targeted. Within the scope of the catheter examination, measurements of the electrical activities in the case of stimulation disturbances can be taken, for example, and there may be the possibility, for example, for direct treatment by ablation of muscular or nerve stimulation paths. For such purposes, the catheter comprises at least one, but generally two or more, electrodes arranged on an outer surface of the catheter, it being possible to take the measurement or to carry out the treatment by means of said electrode(s). Depending on the specific purpose of the diagnosis and/or treatment, there are a large number of adapted variants of catheters of this type; for example, U.S. Pat. No. 5,239,999 presents what is known as an ablation catheter.

The conventional way to produce and contact an electrode on a catheter is to produce said electrode from a metal part, for example, a ring or a plate, which is then connected by means of, for example, soldering, lasering or resistance welding, to a feed wire. The feed wire is then threaded through a hole in the catheter wall into an inner lumen of the catheter shaft and is guided to the proximal end thereof. The metal part is attached distally to the intended point of the catheter shaft by means of gluing, crimping, clamping, or the like. The feed wire is lastly connected at its other end to a plug connector. The conventional production technique is therefore relatively complex and labor-intensive.

U.S. Pat. No. 5,239,999 describes a catheter of which the distal end comprises a helical winding, over which the electrodes together with associated conductive tracks are accommodated. This winding is anchored distally and is wound around the catheter shaft.

The present invention is directed toward overcoming one or more of the above-identified problems.

SUMMARY

One or more known disadvantages of the prior art can be overcome or at least mitigated with the aid of the catheter according to the present invention, in particular, a cardiac catheter or a vascular catheter. The catheter has a film composite structure, which at least comprises:

(i) a polymer film that is shaped such that a first polymer film layer, which is arranged inwardly relative to the catheter, and a second polymer film layer, which is arranged outwardly relative to the catheter, are produced;

(ii) one or more electrodes arranged at least partially on an outer surface of the film composite structure; and (iii) a conductor structure, which comprises conductive tracks for the electrical connection of the electrodes and which is arranged at least in part between the first and second polymer film layers.

The present invention is based on the finding that a catheter equipped with electrodes can be produced particularly easily and reliably if the entire electrode configuration, that is to say electrodes together with associated conductive tracks, is part of a flexible film composite structure produced by means of circuit board technology known per se, wherein the film composite structure simultaneously forms at least parts of the lumen of the catheter shaft. In other words, the film composite structure contains the conductive tracks necessary for electrical connection of the electrodes and also the electrodes themselves. Here, the composite structure comprises at least one inner layer and at least one outer layer. The electrodes are arranged on the outer polymer layer in order to fulfill their intended use. The film composite structure thus itself forms the catheter wall in this region of the catheter, and thus also defines at least the lumen of the catheter. In this way, a very compact structure of the catheter shaft is enabled and, therefore, sufficient installation space for guide wires, cannulas, sensors, etc. is provided in the lumen of the catheter, thus allowing an improved adaptation of the catheter to the respective proposed use. Furthermore, an improved mechanical load-bearing capacity of the catheter is provided by the integration of conductive tracks and electrodes into the film composite structure. Lastly, the manufacturing method of the catheter is substantially simplified and is less susceptible to faults, because only the prefabricated film composite ultimately still has to be placed at the corresponding point and connected to the further components of the catheter in order to form the electrode configuration.

The polymer film is preferably formed from a thermoplastic, in particular, a liquid crystal polymer ("LCP"). Liquid crystal polymers are characterized by mechanical properties that are particularly suitable for the intended purposes. Alternatively, the polymer films may also consist of polyurethane, polyamide or polyether block amides ("PEBA"). The proposed thermoplastics have the advantage that they can be integrally bonded to one another by a direct material-material connection (welding, fusing, flowing into one another, etc.) without the use of additional adhesives.

In accordance with a particularly preferred embodiment of the inventive catheter, the film composite structure, rolled up, therefore forms a lumen of the catheter, wherein the overlapping regions of the film composite structure are interconnected in a sealed manner by means of an integral join (i.e., direct material-material connection).

A further aspect of the present invention relates to an associated method for producing the catheter, said method comprising the following steps:

a) providing a film composite structure that comprises at least: (i) a polymer film, (ii) one or more electrodes arranged on an outer surface of the film composite structure, and (iii) a conductor structure with conductive tracks for electrical connection of the electrodes; and (b) shaping (for example rolling) the film composite structure in such a way that it overlaps itself such that it forms a lumen of the catheter, wherein a polymer film layer that is arranged inwardly relative to the catheter and a polymer film layer that is arranged outwardly relative to the catheter are produced, the electrodes are located at least in part on the outer face, and the overlapping parts of the film composite structure are interconnected in a sealed manner by integral joining.

In accordance with the production method according to the present invention, the previously described film composite structure is rolled or wound to form at least sub-portions of the catheter shaft of the catheter, and overlapping regions of the film composite structure are interconnected in a sealed manner via a connection method. The film composite structure then basically forms the wall of the catheter shaft in this region. In principle, all conventional integral bonding methods for thermoplastic polymers are suitable. It is particularly advantageous, however, if the joining is achieved by fusion welding or etching and without non-volatile join additive (such as, for example, adhesive). Specifically for medical use, an omission of non-volatile join additives is of particular significance, since it has to be ensured that these additives cannot cause any undesired complications in the event of intracorporeal contact. The examinations necessary for this purpose are very time-consuming and cost-intensive however. In addition, such an additive may stiffen the catheter, such that it does not possess the desired flexibility.

In the case of fusion welding, the regions of the film composite structure that are to be interconnected are softened by heat, pressed together, connected to one another, and then cooled again.

For fusion welding without a join additive, the heat energy can be introduced locally by a heat source (for example, heated mold, heating jaws, etc.). The film composite structure can advantageously also be heated by applied or introduced conductive tracks, which are arranged at the points to be fused and through which a current is sent that is converted into heat in the conductive track and thus fuses the carrier film. In other words, the film composite structure preferably comprises applied or introduced conductive tracks, which are arranged on the regions of the film composite structure to be fused by fusion welding. These conductive tracks are used for electrical heating of the regions to be fused. Lastly, the heat energy necessary for the fusion process is also produced by friction (e.g., ultrasonic welding). Here, the parts of the composite to be connected are rubbed against one another so quickly (e.g., at ultrasonic speed) under pressure that the surface of the carrier film melts as a result of the frictional heat produced and the overlapping parts of the carrier film flow into one another and are thus interconnected. Here, it is advantageous if the surface of the carrier film is rough at least at the points to be connected. This can be achieved, for example, by treatment of the relevant surface region with an etching solution. For example, the surface of the LCP can be etched and therefore roughened using Toray's TPE3000, a known etching solution for wet etching of polyimide.

For the fusion of the LCP, temperatures in the range from 250 to 310° C., and usually around 290° C., are generally necessary. For polyurethane and PEBA, temperatures in the range from 140 to 200° C. are generally required.

Alternatively, the joining can be achieved by the etching with a solvent of regions of the film composite structure that are to be connected, the pressing together of the etched regions, and complete removal of the solvent. Here too, it is therefore key that the connection region does not contain further non-volatile join additives; the connection region therefore merely involving the material of which the film composite structure consists.

Solvents that can be used for connection of the overlapping parts of the film composite structure are, in the case of LCP, for example, fluorinated phenols, such as pentafluorophenol, tetrafluorophenol or 3,5-bis(trifluoromethyl)phenol. In the case of polyurethane and PEBA, dimethylformamide, tetrahydrofuran or pyridine can be used as solvent.

A layer thickness of the polymer film is preferably in the range from 10 to 100 µm.

The conductor structure is preferably embedded in an adhesive film for insulation and for protection, and is covered by a second polymer film. This adhesive film may also be formed from a liquid crystal polymer, of which the melting point is selected to be slightly lower, however, than the melting point of the two polymer films to be connected. Alternatively, the conductor structure can be covered by a coating layer.

In the case of the electrode configuration according to the present invention, a thermoplastic biocompatible carrier film (e.g., polymer film) formed from the aforementioned materials is therefore used, to which metal electrode areas are applied or from which metal electrode areas are etched, out or on which metal electrode areas are deposited by means of known circuit board technology in the flat state. The conductive tracks of the conductor structure are preferably formed from copper. The electrodes preferably consist of a highly conductive biocompatible metal material, such as, for example, gold, platinum, platinum/iridium alloys or palladium alloys or comprise at least one coating formed from this metal material(s). In the latter case, copper in particular is used as a base material for the coating.

The electrode configuration is brought into the desired three-dimensional shape, generally rolled as a cylinder, such that at least part of the electrode areas are located on the outer face of the three-dimensional shape and overlap the film composite. The overlapping regions of the film composite, as already described before, are interconnected. The electrodes are preferably formed as ring electrodes.

Further preferred embodiments of the present invention will emerge from the dependent claims and the further description.

Further features, aspects, objects, advantages, and possible applications of the present invention will become apparent from a study of the exemplary embodiments and examples described below, in combination with the Figures, and the appended claims.

DESCRIPTION OF THE DRAWINGS

The present invention will be explained hereinafter on the basis of Figures and an associated exemplary embodiment. In the Figures:

FIG. 3 shows a cross-section through the catheter according to the present invention in the region of the film composite structure;

FIG. 4 shows a schematic illustration of the rolled film composite structure; and FIG. 5 shows a plan view of the distal end of a catheter according to the present invention.

DETAILED DESCRIPTION

Figure 1:
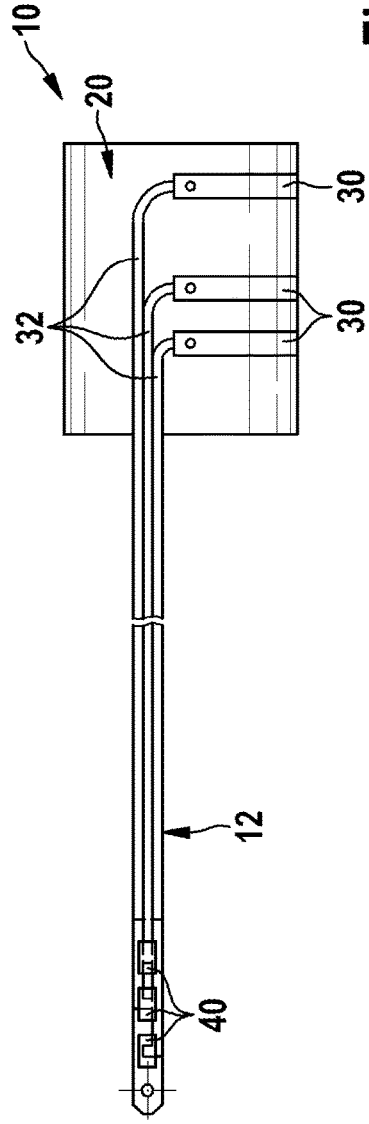
FIG. 1 shows a schematic illustration of an intermediate product for producing a catheter with a distally arranged film composite structure.

FIG. 1 shows a schematic plan view of an intermediate product of the manufacturing process of a catheter. The right-hand part of FIG. 1 shows the region of the distal catheter shaft 10, which is later to carry the electrode configuration. A film composite structure 10 is located in a region of the catheter shaft 10 illustrated here in the rolled state. The film composite structure 20 in the present case has a total of three electrodes 30, which are electrically connected via conductive tracks 32. The conductive tracks 32 are guided to the proximal end of the catheter shaft 10 (left-hand part of FIG. 1) and are connected to suitable contact areas 40. The proximal part 12 of the catheter shaft 10 may also be formed from the film composite structure 20. In other words, the film composite structure 20 can extend over the entire region of the electrode configuration together with conductive tracks 32 as far as the proximal connector points of the conductive tracks 32 on the further component parts of the electrical circuit (e.g., plug connections).

Figure 2:
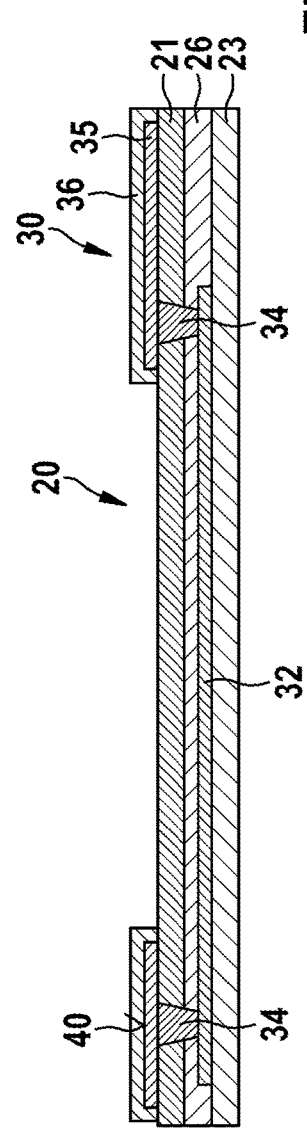
FIG. 2 shows a longitudinal section through the catheter according to the present invention in the region of the film composite structure.

FIG. 2, again purely schematically, illustrates a longitudinal section through an embodiment of the film composite structure 20 with an electrode 30, a conductive track 32 and a proximal contact area 40. In accordance with this exemplary embodiment, the film composite structure 20 comprises a first polymer film 21 forming the outer surface of the catheter shaft, and a second, covering polymer film 23. An adhesive layer 26, into which a conductive track 32 is integrated and which connects the two polymer films 21, 23, is located between the two polymer films 21, 23.

The conductive track 32 is connected by means of a feedthrough 34 to the electrode 30 arranged outwardly on the first polymer film 21. The electrode 30 is formed in two layers in the present case, with a lower layer 35 formed from, for example, copper and an upper layer 36 applied thereto, formed from, for example, gold and forming the actual electrode area. The conductive track 32 also consists of, for example, copper in the present case.

The two polymer films 21, 23, and also the adhesive film 26, are produced in accordance with the exemplary embodiment on the basis of a liquid crystal polymer, wherein the adhesive film 26 is modified such that it softens at a lower temperature and thus allows a lamination of the two polymer films 21, 23. All three film layers 21, 23 and 26 have a layer thickness in the present case of approximately 25 µm. The conductive track 32 has a layer thickness of approximately 16 µm. The lower layer 35 of the electrode 30 has a layer thickness of approximately 5 to 7 µm, and the upper layer 36 formed from, for example, gold has a layer thickness of approximately 3 to 4 µm. Of course, other thicknesses for the layers are contemplated.

In a simplified embodiment, the film composite structure may also consist merely of a polymer film 21, such that the second polymer film 23 and also the adhesive layer 26 are omitted. In such a simplified embodiment, the conductive track 32 can be arranged on the same side of the polymer film 21 as the electrode 30. Alternatively, the conductive track 32 can be arranged on the rear side of the polymer film 21 and can be connected via a feedthrough 34 to the electrode 30 arranged on the front side of the polymer film 21. The proximal contact area 40 can also be arranged on the same side of the polymer film 21 as the conductive track 32, or can be connected via a feedthrough 34 on the other side of the polymer film 21.

FIG. 3 shows a cross-section through the catheter shaft of the catheter in the region of the film composite structure 20. The composite structure 20 is rolled such that regions overlap. In the present example, two whorls are formed, such that an inner polymer film layer 22 and an outer polymer film layer 24 are produced, and the overlap region is one full whorl. Due to a suitable integral joining method, the two polymer film layers 22, 24 are interconnected in a sealed manner in at least parts of the overlap region, but in particular at the edge 50 of the outer polymer film layer 24.

The connection is produced in accordance with the present example by, for example, a fusion welding method without use of a further join additive.

FIG. 4 shows a part of the catheter shaft 10 of the catheter in the region of the film composite structure 20. As can be seen, the electrodes 30 are formed as ring electrodes. The conductive tracks 32 (not visible here) are arranged inside the film composite structure 20 and are continued via an extension 60. It can be seen that sufficient space for further catheter components remains inside the lumen of the catheter shaft.

FIG. 5 again shows the distal end 70 of the catheter shaft 10 of the catheter according to the present invention. The film composite structure 20, with its integrated ring electrodes 30, can be seen. The distal end 70 of the catheter shaft can be brought into a curved shape by a thermal process, for example.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. A catheter with a film composite structure, said catheter comprising:
   (i) a polymer film that is shaped such that a first polymer film layer, which is arranged inwardly relative to the catheter, and a second polymer film layer, which is arranged outwardly relative to the catheter, are produced;
   (ii) one or more electrodes arranged at least partially on an outer surface of the second polymer film layer; and
   (iii) a conductor structure comprising conductive tracks for electrical connection of the one or more electrodes and which is arranged at least in part between the first and second polymer film layers, wherein the first polymer film layer, second polymer film layer, one or more electrodes and conductor structure form the film composite structure, and wherein the film composite structure, when rolled, forms a lumen of the catheter, wherein overlapping regions of the film composite structure are interconnected in a sealed manner by an integral join, wherein the film composite structure is rolled such that the overlap between the first polymer film layer and the second polymer film layer is at least one whorl.

2. The catheter as claimed in claim 1, wherein the integral join does not contain any join additive.

3. The catheter as claimed in claim 1, wherein the polymer film is formed from a thermoplastic.

4. The catheter as claimed in claim 3, wherein the thermoplastic comprises a liquid crystal polymer, a polyurethane, a polyamide, and/or a polyether block amide.

5. The catheter as claimed in claim 1, wherein a layer thickness of the first and second polymer film layers combined is in the range from 10 to 100 μm.

6. The catheter as claimed in claim 1, wherein the conductor structure is embedded in an adhesive film layer connecting the first polymer film and the second polymer film layer.

7. The catheter as claimed in claim 1, wherein the conductor structure is covered by a coating layer.

8. The catheter as claimed in claim 1, wherein the conductive tracks are formed from copper.

9. The catheter as claimed in claim 1, wherein at least one of the one or more electrodes consist of a highly conductive biocompatible metal material selected from gold, platinum, platinum/iridium alloys or palladium alloys.

10. The catheter as claimed in claim 1, wherein at least one of the one or more electrodes comprise a coating formed from a highly conductive biocompatible metal material selected from gold, platinum, platinum/iridium alloys or palladium alloys.

11. The catheter as claimed in claim 1, wherein at least one of the one or more electrodes is formed as a ring electrode.

12. A method for producing a catheter, said method comprising the following steps:
   a) providing a film composite structure that comprises: (i) a first polymer film layer and a second polymer film layer, (ii) one or more electrodes arranged at least partially on an outer surface of the second polymer film layer, and (iii) a conductor structure comprising conductive tracks for electrical connection of the one or more electrodes, and which is arranged at least in part between the first and second polymer film layers; and
   b) rolling the film composite structure in such a way that it overlaps itself such that it forms a lumen of the catheter, wherein the first polymer film layer is arranged inwardly relative to the catheter and the second polymer film layer is arranged outwardly relative to the catheter are produced, the electrodes are located at least in part on an outer face, and the overlapping parts of the film composite structure are interconnected in a sealed manner by integral joining, wherein the film composite structure is rolled such that the overlap between the first polymer film layer and the second polymer film layer is at least one whorl.

13. The method as claimed in claim 12, wherein the integral joining is achieved by fusion welding and without join additive.

14. The method as claimed in claim 13, wherein the integral joining is achieved by local introduction of heat energy by means of a heat source.

15. The method as claimed in claim 13, wherein the integral joining is achieved by ultrasonic welding.

16. The method as claimed in claim 13, wherein the film composite structure further comprises applied or introduced additional conductive tracks, which are arranged on regions of the film composite structure to be fused by fusion welding, and wherein the additional conductive tracks are used for electrical heating of the regions to be fused.

17. The method according to claim 12, wherein the integral joining is achieved by etching with a solvent regions of the film composite structure that are to be connected, pressing together the etched regions, and completely removing the solvent.

\* \* \* \* \*